United States Patent [19]
Reddy et al.

[11] Patent Number: 5,783,684
[45] Date of Patent: Jul. 21, 1998

[54] OXIDIZING REAGENT FOR USE IN OLIGONUCLEOTIDE SYNTHESIS

[75] Inventors: Meda Parameswara Reddy; Firdous Farooqui, both of Brea; Maged A. Michael, Placentia, all of Calif.

[73] Assignee: Beckman Instruments, Inc., Fullerton, Calif.

[21] Appl. No.: 526,184

[22] Filed: Sep. 11, 1995

[51] Int. Cl.$^6$ .................................................. C07H 1/00
[52] U.S. Cl. .................. 536/25.3; 536/25.31; 423/462; 423/466; 423/486; 423/499.1; 423/500; 423/502
[58] Field of Search .................. 423/500, 462, 423/466, 486, 499.1, 502; 536/25.3, 25.31

[56] References Cited

PUBLICATIONS

Gait, M. J. "Oligonucleotide Synthesis a Practical Approach", IRL Press, p. 50, 1985.

Matteucci, M.D. & Caruthers, M.H., "The Synthesis of Oligodeoxpyrimidines on a Polymer Support", Tetrahedron Letters, vol.. 21, pp. 719–722.

Ogilvie, K. K. & Nemer, M.J., "The Synthesis of Phosphite Analogues of Ribonucleotides"; Tetrahedron Letters, vol. 21, pp.4145–4148.

Ogilvie, K. K. & Nemer, Mona J., "Silica Gel As Solid Support in the Synthesis of Oligoribonucleotides", Tetrahedron Letters, vol. 21, pp. 4159–4161.

*Primary Examiner*—James O. Wilson
*Attorney, Agent, or Firm*—William H. May; P. R. Harder; Robbins, Berliner & Carson, LLP

[57] ABSTRACT

Oxidizing compositions particularly for use in automated oligonucleotide synthesis containing a mixture of KI and $I_2$ in solution, in equilibrium with $KI_3$. One preferred composition contains 1.75% $KI_3$ (providing 0.69% KI and 1.06% $I_2$) in tetrahydrofuran/pyridine/water (93/5/2, v/v). These formulations enable synthesis of oligonucleotides of significantly higher quality than the currently employed formulation comprising 3% $I_2$ in tetrahydrofuran/pyridine/water (74/21/2, v/v).

7 Claims, 4 Drawing Sheets

OXIDIZING REAGENT FOR USE IN OLIGONUCLEOTIDE SYNTHESIS

BACKGROUND OF THE INVENTION

This invention relates generally to the field of chemistry. More particularly, the present invention relates to compositions and methods for use in automated synthesis of oligonucleotides.

DNA synthesis primarily involves sequential assembling of nucleotides on an insoluble solid support. Phosphoramidite chemistry is the most widely used coupling chemistry and the oxidation reaction is one of the important chemical steps in every synthesis cycle.

DNA Synthesis Cycle

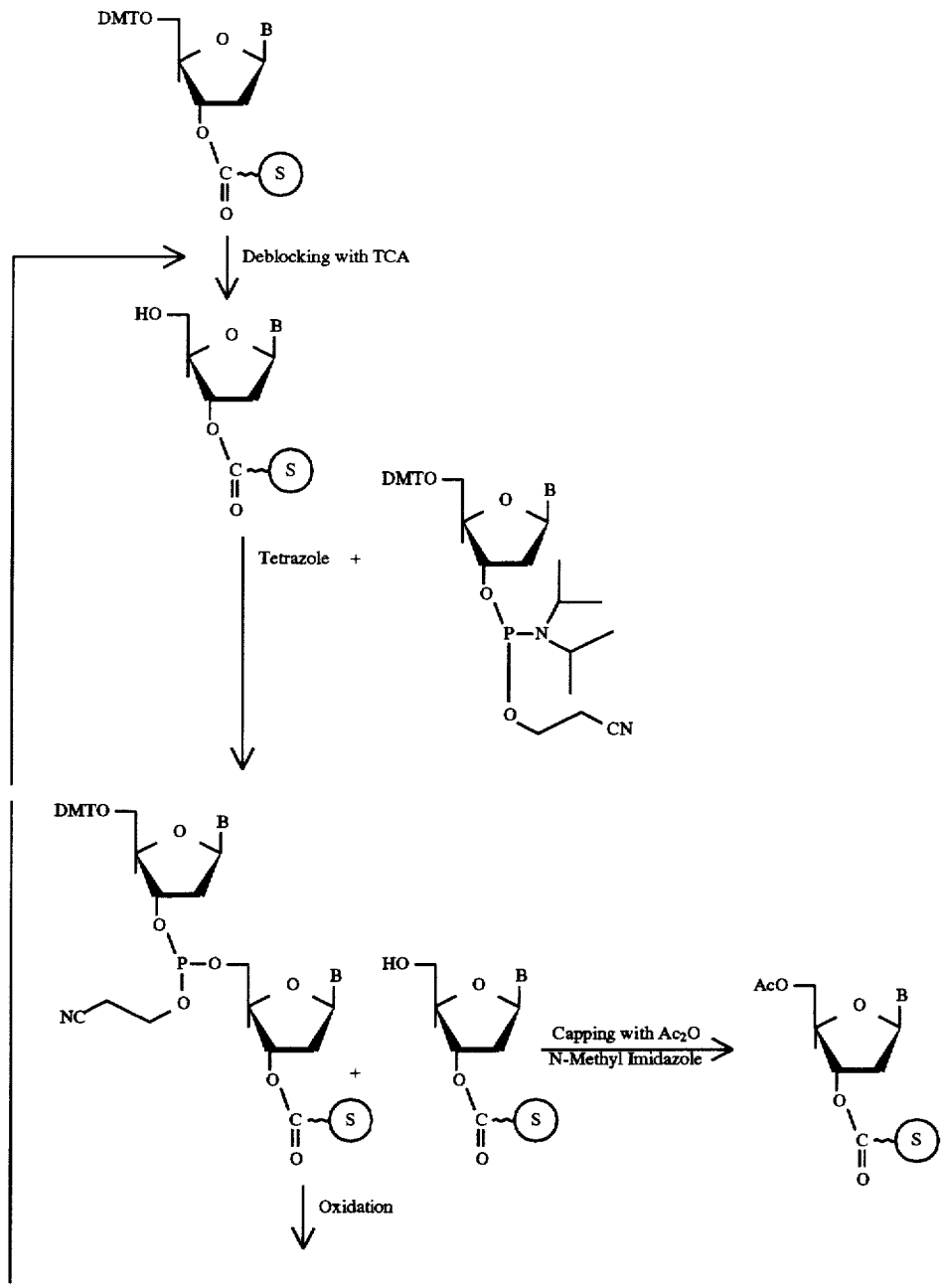

-continued
DNA Synthesis Cycle

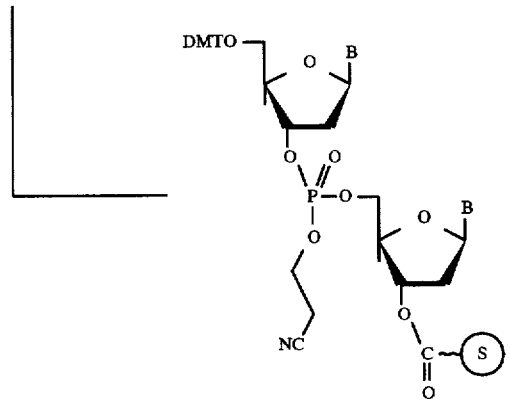

At present, 3% iodine in tetrahydrofuran/pyridine/water (74/21/2, w/w) is employed as the oxidizing agent in some automated oligonucleotide synthesizers, such as the Beckman® Oligo 1000 and Oligo 1000M synthesizers. However, it has been determined that this formulation is detrimental to the stability of oligonucleotides, especially of the trivalent internucleotide phosphorous intermediate formed transiently during oligonucleotide synthesis.

Optimization of the iodine formulation led to a 0.3% iodine in tetrahydrofuran/pyridine/water (93/5/2, v/v) as an efficient reagent; this reagent also provided an improved quality oligonucleotide product. However, this formulation was found not to be compatible with some automated oligonucleotide synthesizers, such as the Oligo 1000 synthesizer (Beckman Instruments, Fullerton, Calif.). In particular, the Oligo 1000 synthesizer utilizes the absorbance of iodine to calibrate the instrument; 0.3% iodine did not provide the absorbance which was required.

Introducing acridine (0.03%) orange dye as an inert additive into the formulation maintained a higher quality of oligonucleotides without any negative effects. As acridine orange is known to be a DNA intercalator, however, this approach is not entirely satisfactory.

There thus remains a need for an oxidizing solution which is safe and efficient for use in automated oligonucleotide synthesizers.

It is an object of the present invention to provide compositions and methods which do not suffer from the drawbacks of the heretofore-known compositions.

SUMMARY OF THE INVENTION

In accordance with the present invention, there are provided oxidizing compositions for use in automated oligonucleotide synthesis comprising a mixture of KI and $I_2$ in solution. One preferred composition comprises 1.75% $KI_3$ (providing 0.69%KI and 1.06 % $I_2$) in tetrahydrofuran/pyridine/water (93/5/2, v/v). These formulations enable synthesis of oligonucleotides of significantly higher quality than the currently employed formulation comprising 3% $I_2$ in tetrahydrofuran/pyridine/water (74/21/2, v/v).

BRIEF DESCRIPTION OF THE DRAWINGS

The invention may be better understood with reference to the accompanying drawings, in which.

DETAILED DESCRIPTION OF THE INVENTION

The formulations of the present invention provide significant advantages relative to prior art formulations. The oligonucleotides synthesized using the inventive oxidizing agents are substantially higher in quality than products obtained using prior art formulations; thus, there is a higher percentage of the desired full length sequences and a lower percentage of shorter failure sequences when using a reagent in accordance with the present invention. Further, these formulations are totally compatible with automated oligonucleotide synthesizers, such as the Beckman® Oligo 1000. In addition, the formulations are stable during storage and in use on the instrument.

$KI_3$ is in equilibrium with $KI+I_3$. At a given time only about 0.3% of $I_2$ is present in the active form, whereas the rest of the $I_2$ is present in the $KI_3$ form (which is non-detrimental to DNA). Moreover, the absorbance of $KI_3$ makes it compatible with the diagnostic features of automated oligonucleotide synthesizers, such as the Oligo 1000. Suitably, $KI_3$ may be generated in situ as hereinafter described. In any event, for purposes of the present invention $KI_3$ is the equivalent of a corresponding mixture of KI and $I_2$.

In preferred formulations of the invention, the solution comprises the equivalent of about 1% to about 3% $KI_3$, more preferably about 1.3% to about 2% $KI_3$. Similarly, the ratio of the components in the tetrahydrofuran/pyridine/water mixture may be varied significantly: the percentage of tetrahydrofuran may be varied within the range of about 50% to about 98%, the pyridine from 1% to 40%, and the water from 0.5% to 30%. The current preferred formulation comprises 1.75% $KI_3$ in tetrahydrofuran/pyridine/water (93/5/2, v/v); this corresponds to a solution comprising 0.69% KI and 1.06% $I_2$.

Figure 1A:
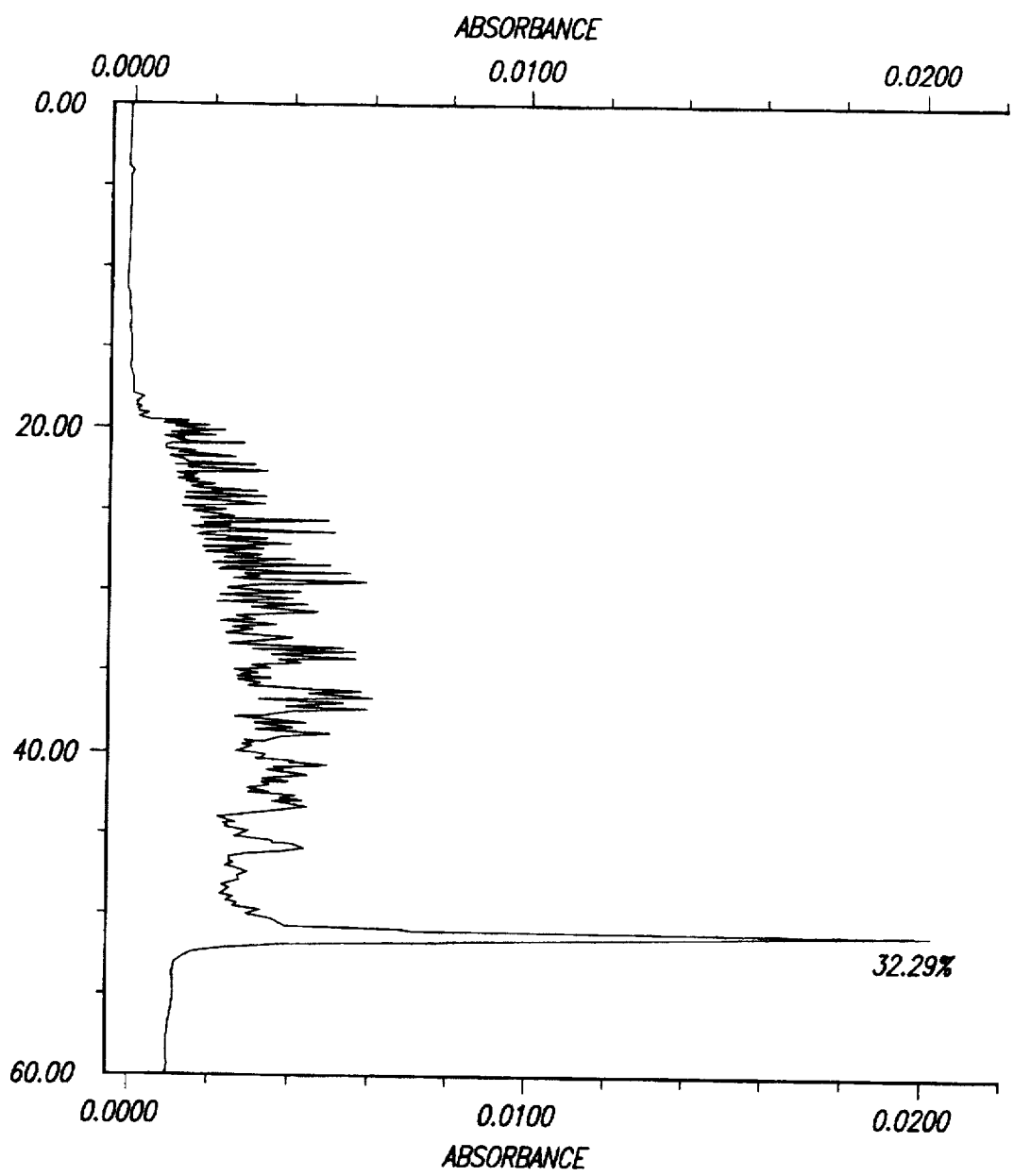
FIGS. 1A and 1B illustrate the results of gel filled capillary electrophoresis of 101 mers prepared using the prior art (1A) and inventive (1B) oxidizing agents, respectively.
Figure 2A:
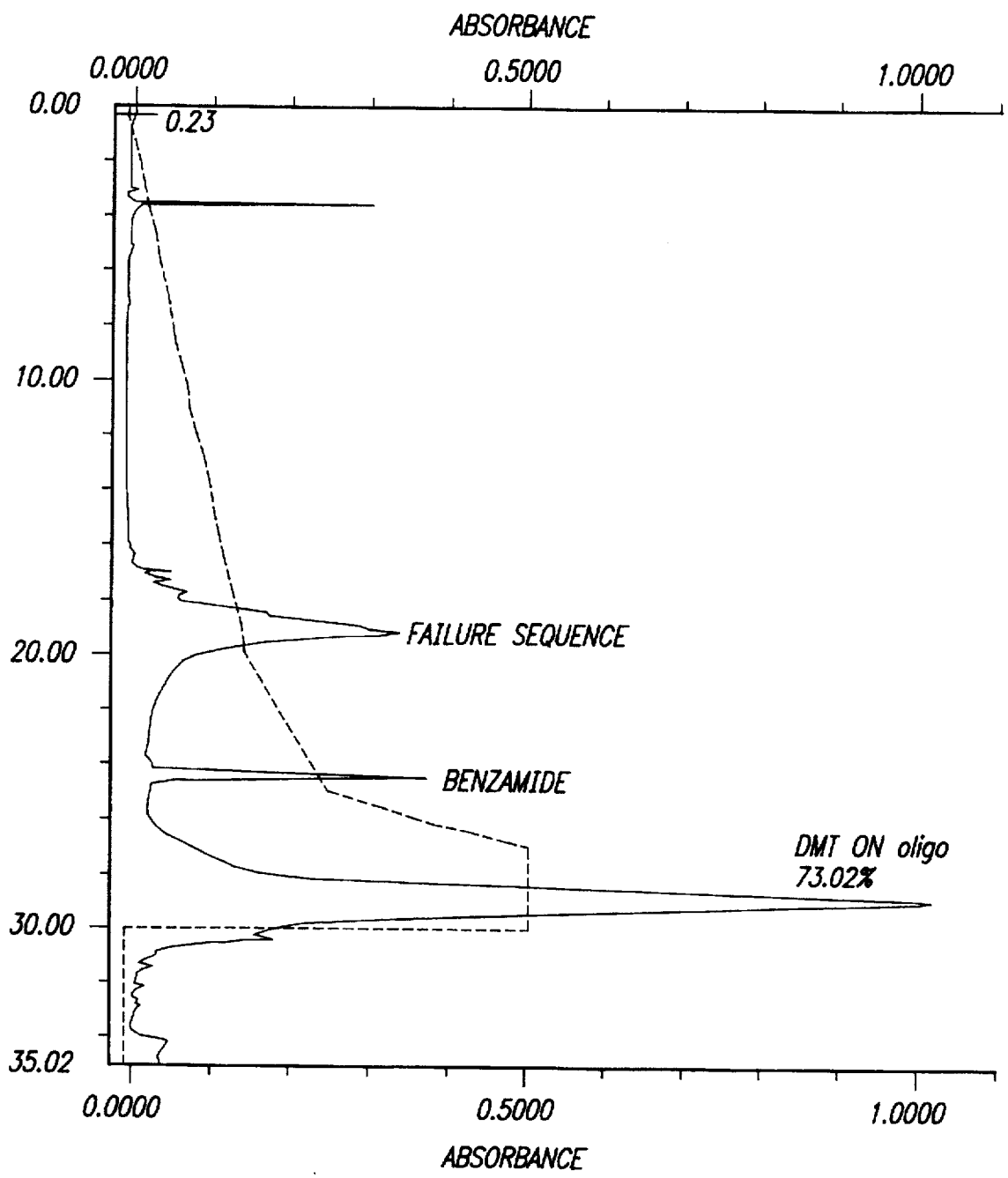
FIGS. 2A and 2B illustrate reverse phase HPLC results for 35 mers prepared using the prior art (2A) and inventive (2B) oxidizing agents, respectively.
Figure 2B:
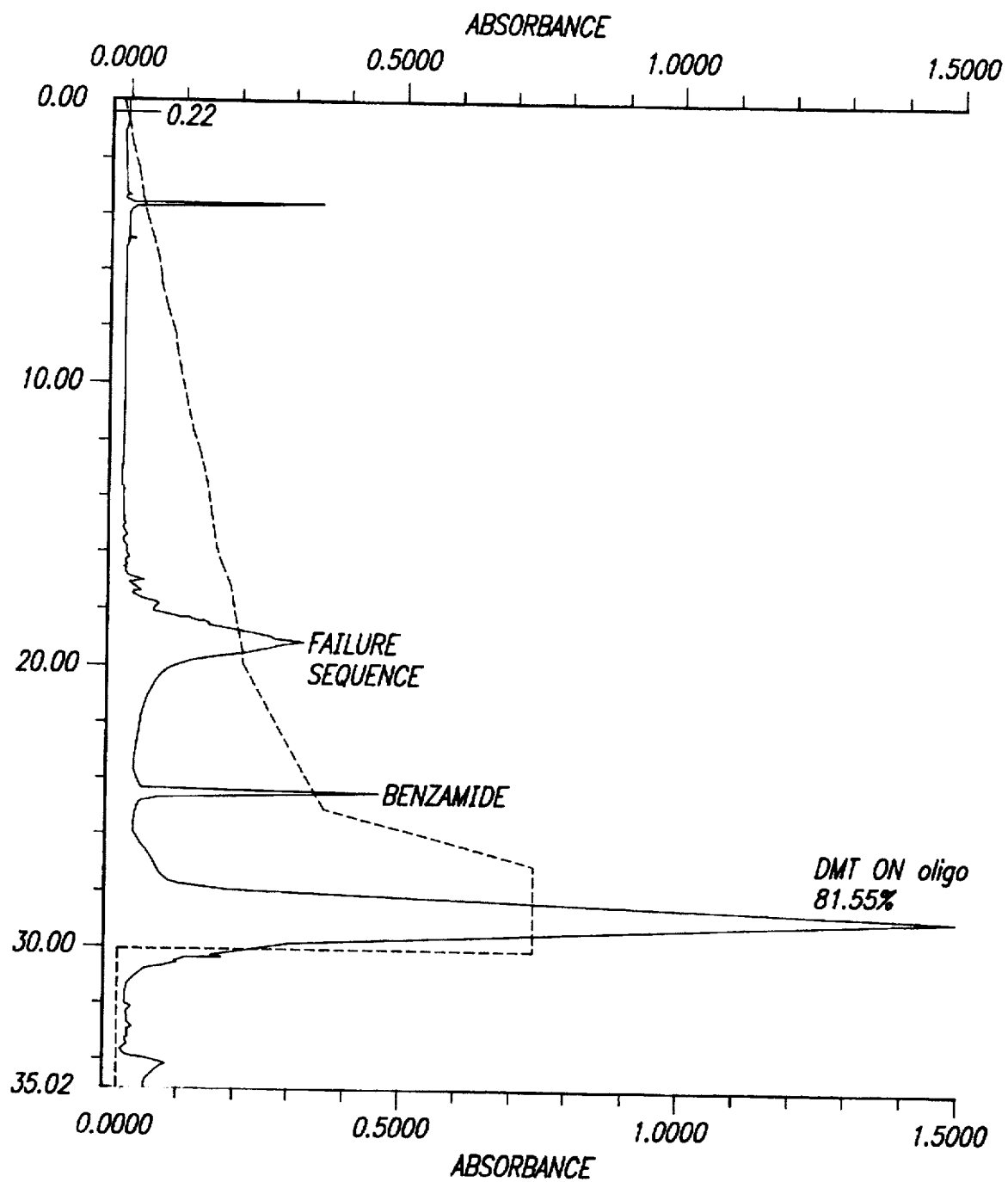

The preferred formulation showed consistently superior performance relative to the heretofore known formulation generally employed with automated oligonucleotide synthesizers such as the Beckman Oligo 1000 and Oligo 1000M. FIGS. 1A (prior art) and 1B (invention) demonstrate this superior performance by providing a comparison of 101 mers as analyzed by gel filled capillary electrophoresis;

FIGS. 2A (prior art) and 2B (invention) similarly provide a comparison of 35 mers as analyzed by reverse phase HPLC. An accelerated stability study showed the expected stability.

The invention may be better understood with reference to the accompanying examples, which are intended for purposes of illustration only and should not be construed as in any sense limiting the scope of the invention as defined in the claims appended hereto.

Example 1

For preparation of an exemplary oxidizer formulation in accordance with the present invention, commercially-available agents as purchased and double-distilled water were employed. 6.9 g of potassium iodide was dissolved in 20 ml of water. 10.6 g of iodine was dissolved in 930 ml of tetrahydrofuran and 50 ml of pyridine. Both solutions were mixed and the mixture shaken for 1–2 minutes. This produced a solution of approximately 1.75% $KI_3$ (In equilibrium with $KI + I_2$) in THF/pyridine/water (93/5/2, v/v).

Example 2

Figure 1B:
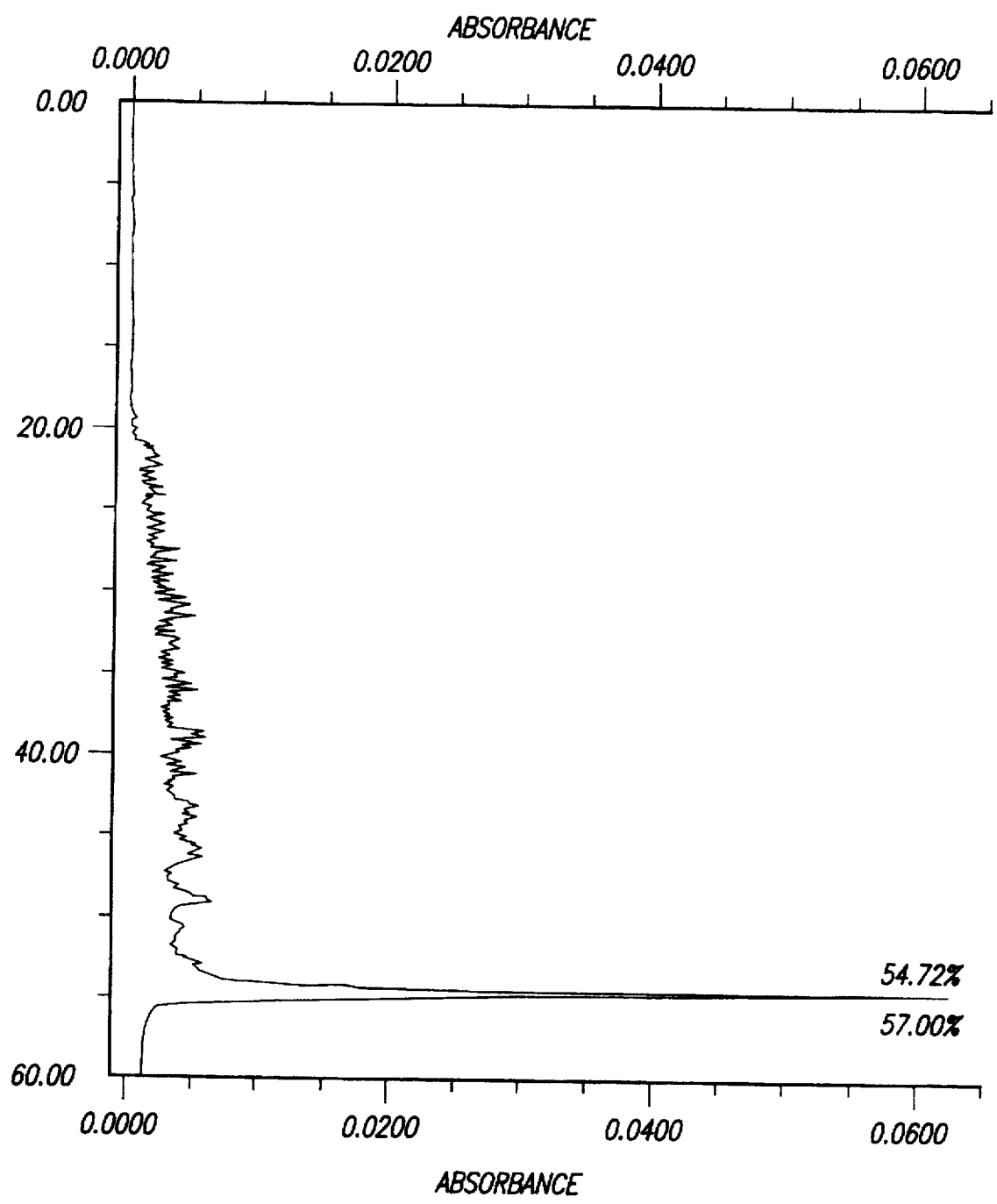

Capillary Electrophoresis (CE) was run on the Beckman® P/ACE 2000 on 101 mers synthesized using an oxidizing solution according to the prior art and one in accordance with the present invention. The 101 mers had the following sequence: 5'AAC-GTC-GGT-AAC-GTA-CAC-GGT-AGC-TAC-GGA-CAC-CGT-GGC-AAT-ACG-ACA-GGT-AAC-CTG-TGG-AAC-GTA-CAC-GGA-AGA-GAC-TAG-GGA-TGG-GAG-TAC-GGA-TGG- GT3' (Seq. ID No. 1). The capillary gel column (Beckman, V100P Urea Gel Column) was loaded and cut to 37 cm long. Tris-Borate, 7 M Urea buffer (Beckman, Gel Buffer Kit) was used according to directions. The absorbances of oligonucleotides were in the range of 0.05 to 2 OD 260 nm/mL, depending upon the quality and length of oligonucleotide. Injection was at 10 kv for 3 sec, while separation was at 11 kv for 30–60 min, depending upon the length. The results for oligonucleotides prepared using the prior art and inventive oxidizing agents are shown in FIGS. 1A and 1B, respectively.

Example 3

Reverse Phase HPLC separates the desired oligonucleotide which is expected to carry a lipophilic dimethoxytrityl (DMT) group from the failure sequences which are not expected to carry the DMT group. 35 mers were synthesized using the prior art and inventive formulations with the 5'-terminal DMT group left on. The 35 mers had the following sequence: 5'GAT-GCC-AGT-TCG-GTC-ATA-CAC-GTA-CTA-CGA-CT3'. The oligonucleotides were cleaved and deprotected with ammonia. Both of these oligonucleotides were analyzed by reverse phase HPLC following the conditions described below:

| HPLC column: | $C_{18}$ microsorb (Rainin Cat. #86-200-C5) 5µ particles, 4.6 × 25 mm |
|---|---|
| Bottle A: | 0.1 M Ammonium acetate, pH 6.9 |
| Bottle B: | Acetonitrile |
| Program: | Flow rate, 1 ml/min |
| | 0–20 min gradient to 15% B |
| | 20–25 min gradient to 25% B |
| | 25–27 min gradient to 50% B |
| | 27–30 min at 50% B |
| | 30–35 min at 0% B |

Results of HPLC analysis are shown in FIGS. 2A (prior art) and 2B (invention).

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 101 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: no ( i v ) ANTI-SENSE: no ( x i ) SEQUENCE DESCRIPTION: SEQ ID NO:1:

| AAC | GTC | GGT | AAC | GTA | CAC | GGT | AGC | TAC | GGA | CAC | CGT | 3 6 |
|---|---|---|---|---|---|---|---|---|---|---|---|---|
| GGC | AAT | ACG | ACA | GGT | AAC | CTG | TGG | AAC | GTA | CAC | GGA | 7 2 |
| AGA | GAC | TAG | GGA | TGG | GAG | TAC | GGA | TGG | GT | | | 1 0 1 |

What is claimed is:

1. An oxidizing iodine-containing composition for use in oligonucleotide synthesis comprising a combination of KI and $I_2$ in a solution to provide a source of iodine.

2. The composition according to claim 1, wherein the solution of KI and $I_2$ are in equilibrium with $KI_3$.

3. The composition according to claim 2, comprising about 1% to about 3% $KI_3$.

4. The composition according to claim 3, comprising about 1.3% to about 2% $KI_3$.

5. The composition according to claim 1, wherein the solution comprises tetrahydrofuran/pyridine/water.

6. The composition according to claim 5, wherein the solution comprises 50% to 98% tetrahydrofuran, 1% to 40% pyridine and 0.5% to 30% water.

7. The composition according to claim 1, comprising 0.69% KI and 1.06% $I_2$ in tetrahydrofuran/pyridine/water (93/5/2, v/v).

* * * * *